(12) United States Patent
Shinhama

(10) Patent No.: US 7,569,702 B2
(45) Date of Patent: Aug. 4, 2009

(54) METHOD FOR PRODUCING 4-NITROIMIDAZOLE COMPOUND

(75) Inventor: Koichi Shinhama, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 342 days.

(21) Appl. No.: 10/589,864

(22) PCT Filed: Feb. 15, 2005

(86) PCT No.: PCT/JP2005/002668

§ 371 (c)(1),
(2), (4) Date: Aug. 17, 2006

(87) PCT Pub. No.: WO2005/077913

PCT Pub. Date: Aug. 25, 2005

(65) Prior Publication Data

US 2007/0161802 A1 Jul. 12, 2007

(30) Foreign Application Priority Data

Feb. 18, 2004 (JP) .............................. 2004-041381
Sep. 27, 2004 (JP) .............................. 2004-278999

(51) Int. Cl.
*C07D 233/68* (2006.01)
*C07D 233/91* (2006.01)
*A61K 31/4164* (2006.01)

(52) U.S. Cl. .................................... 548/327.1; 514/398

(58) Field of Classification Search .............. 548/327.1; 514/398

See application file for complete search history.

(56) References Cited

U.S. PATENT DOCUMENTS 3,341,548 A 9/1967 Hoffer

FOREIGN PATENT DOCUMENTS

WO WO 97/01562 1/1997
WO WO 2004/033463 A1 4/2004
WO WO 2004/035547 A1 4/2004

OTHER PUBLICATIONS

Suwinski, J. et al., "Nitroimidazoles, Part V*, Chloronitroimidazoles From DinitroimiDazoles, A Reinvestigation**," Polish Journal of Chemistry, vol. 56, pp. 1261-1272, (1982).*
Nagarajan, K. et al., "Nitroimidazoles XXI** 2,3-Dihydro-6-Nitroimidazo [2,1-*b*] Oxazoles with Antitubercular Activity***," Eur. J. Med. Chem., vol. 24, pp. 631-633, (1989).
Stover, C. K. et al., "A Small-Molecule Nitroimidazopyran Drug Candidate for the Treatment of Tuberculosis," Nature, vol. 405, pp. 962-966, (Jun. 22, 2000).
Sehgal, R. K. et al., "Potential Radiosensitizing Agents. 2. Synthesis and Biological Activity of Derivatives of Dinitroimidazole with Oxiranes," J. Med. Chem., vol. 24, pp. 601-604, (1981).
Ashtekar, D. R. et al., "In Vitro and In Vivo Activities of the Nitroimidazole CGI 17341 against *Mycobacterium Tuberculosis*," Antimicrobial Agents and Chemotherapy, vol. 37, No. 2, pp. 183-186, (Feb. 1993).

* cited by examiner

*Primary Examiner*—Rei-Tsang Shiao
*Assistant Examiner*—Janet L Coppins
(74) *Attorney, Agent, or Firm*—Finnegan, Henderson, Farabow, Garrett & Dunner, L.L.P.

(57) ABSTRACT

The present invention provides a method for producing a 4-nitroimidazole compound represented by general formula (1) at high yield and at high purity by a safe method causing few dangers such as explosion. The production method of the present invention comprises iodinating a 4-nitroimidazole compound represented by general formula (2): wherein each of $X^1$ and $X^2$ represents a chlorine atom or bromine atom, and then reducing the obtained 5-iodo-4-nitroimidazole compound represented by general formula (3): wherein $X^2$ is the same as defined above.

(1)

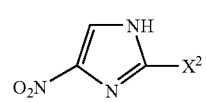

9 Claims, No Drawings

METHOD FOR PRODUCING 4-NITROIMIDAZOLE COMPOUND

TECHNICAL FIELD

The present invention relates to a method for producing a 4-nitroimidazole compound.

BACKGROUND ART

A 4-nitroimidazole compound represented by the following general formula (1):

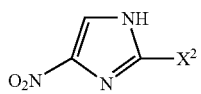
(1)

wherein $X^2$ represents a chlorine atom or bromine atom, is useful as a synthetic intermediate used for producing various pharmaceuticals and agricultural chemicals, and particularly used for producing antitubercular agents.

For example, methods represented by the following Reaction scheme-1 and -2 have previously been known as methods for producing the 4-nitroimidazole compound represented by general formula (1) (Jerzy Suwinski, Ewa Salwinska, Jan Watras, and Maria Widel, Polish Journal of Chemistry, 56, 1261-1272 (1982)).

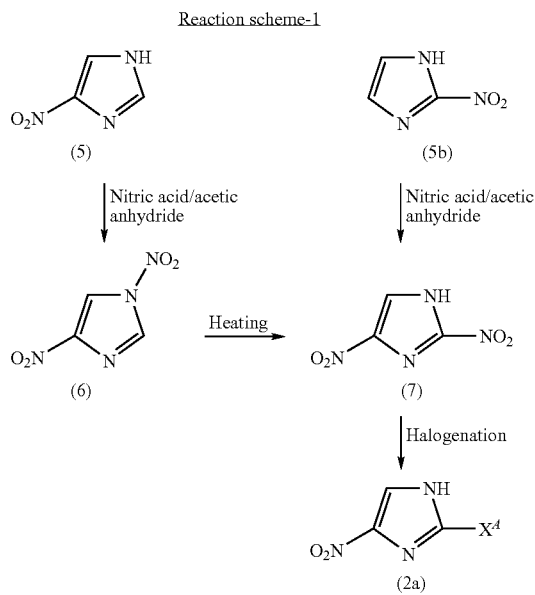

Reaction scheme-2

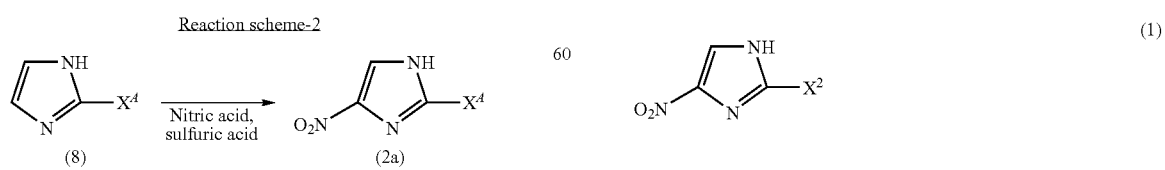

wherein $X^A$ represents a halogen atom.

However, these methods have various disadvantages, and thus, are not adequate as production methods that are industrially applied.

For example, in the method represented by Reaction scheme-1, compounds (6) and (7) that are reaction intermediates are chemically unstable, and there is a risk that these compounds may explode due to impacts such as fall or friction. In addition, in this method, the temperature applied during the reaction to obtain the compound (7) from the compound (6) by heating (approximately 130° C.) exceeds the TNR (Temperature of No Return; the maximal temperature ranging from 60° C. to 70° C., at which the compound can safely be handled in a chemical processing apparatus) of the compound (6). Thus, it has been extremely dangerous to industrially produce the compound of interest in high volume by this method.

The method represented by Reaction scheme-2 involves a reaction of nitrating the compound (8). However, the compound (1a) can be obtained only at low yield by such nitration, and thus, this method is industrially disadvantageous.

DISCLOSURE OF THE INVENTION

It is an object of the present invention to provide a method for producing a 4-nitroimidazole compound represented by general formula (1) at high yield and at high purity by a safer method causing few dangers such as explosion.

In order to achieve the aforementioned object, the present inventors have conducted intensive studies regarding a method for producing a 4-nitroimidazole compound represented by general formula (1). As a result, the present inventors have found that the aforementioned object can be achieved by selectively substituting a chlorine atom or bromine atom at position 5 of a 4-nitroimidazole compound represented by general formula (2) indicated below with an iodine atom, and then selectively reducing position 5 of the obtained 5-iodo-4-nitroimidazole compound represented by general formula (3) indicated below. That is to say, the present inventors have found that a 4-nitroimidazole compound represented by general formula (1) can be produced at high yield and at high purity by a safe method causing few dangers such as explosion, which comprises selectively substituting a chlorine atom or bromine atom at position 5 of a 4-nitroimidazole compound represented by general formula (2) indicated below with an iodine atom, and then selectively reducing position 5 of the obtained 5-iodo-4-nitroimidazole compound represented by general formula (3) indicated below.

The present invention has been completed based on these findings.

1. The present invention provides a method for producing a 4-nitroimidazole compound represented by general formula (1):

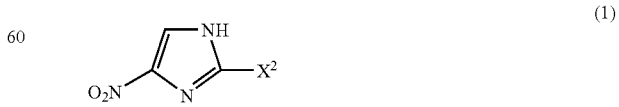
(1)

wherein $X^2$ represents a chlorine atom or bromine atom, comprising iodinating a 4-nitroimidazole compound represented by general formula (2):

(2)

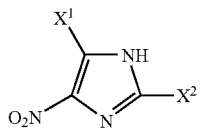

wherein each of $X^1$ and $X^2$ represents a chlorine atom or bromine atom, and then reducing the obtained 5-iodo-4-nitroimidazole compound represented by general formula (3):

(3)

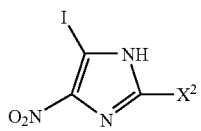

wherein $X^2$ is the same as defined above.

2. The present invention provides, in the above production method, a method for producing a 4-nitroimidazole compound, wherein an iodinating agent is a halogen molecule, hydriodic acid, or a metal salt of hydriodic acid.
3. The present invention provides, in the above production method, a method for producing a 4-nitroimidazole compound, wherein the metal salt of hydriodic acid is sodium iodide, potassium iodide, lithium iodide, zinc iodide, magnesium iodide, or aluminum iodide.
4. The present invention provides, in the above production method, a method for producing a 4-nitroimidazole compound, wherein the iodinating agent is used to the compound (2) at a molar ratio between 1.5:1 and 15:1, and the iodinating agent is sodium iodide.
5. The present invention provides, in the above production method, a method for producing a 4-nitroimidazole compound, wherein the reaction is carried out in the presence of a phase-transfer catalyst.
6. The present invention provides, in the above production method, a method for producing a 4-nitroimidazole compound, wherein the phase-transfer catalyst is used to the compound (2) at a molar ratio between 0.01:1 and 1:1, and the phase-transfer catalyst is a quaternary ammonium salt, phosphonium salt, or pyridinium salt.
7. The present invention provides, in the above production method, a method for producing a 4-nitroimidazole compound, wherein the reducing agent is a hydrogenation reducing agent, and the reducing agent is used to the compound (3) at a molar ratio between 1:1 and 10:1.
8. The present invention provides, in the above production method, a method for producing a 4-nitroimidazole compound, wherein the reducing agent is a catalytic hydrogenation reducing agent, and the reducing agent is used to the compound (3) at a weight ratio between 0.1% by weight and 40% by weight.
9. The present invention provides, in the above production method, a method for producing a 4-nitroimidazole compound, wherein the reaction is carried out in the presence of triethylamine, trimethylamine, or N-ethyldiisopropylamine.

BEST MODE FOR CARRYING OUT THE INVENTION

The method for producing a 4-nitroimidazole compound represented by general formula (1) of the present invention will be described below.

Reaction scheme-3

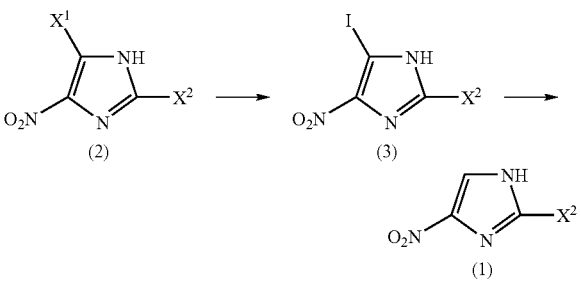

wherein $X^1$ and $X^2$ are the same as defined above.

In the above Reaction scheme-3, the reaction to obtain compound (3) from the compound (2) can be carried out in a suitable solvent in the presence of an iodinating agent.

As an iodinating agent, known iodinating agents can widely be used. Examples of such an iodinating agent may include a halogen atom such as iodine, hydriodic acid, and metal salts of hydriodic acid such as sodium iodide, potassium iodide, lithium iodide, zinc iodide, magnesium iodide, or aluminum iodide. Of these, sodium iodide is preferable. Such an iodinating agent is used to the compound (2), generally at an excessive amount, and preferably at a molar ratio between 1.5:1 and 15:1.

Examples of a solvent may include: water; alcohols such as methanol, ethanol, or isopropanol; ketones such as acetone; acetonitrile; halogenated hydrocarbons such as dichloromethane, dichloroethane, chloroform, or carbon tetrachloride; aromatic hydrocarbons such as benzene, toluene, or xylene; esters such as methyl acetate or ethyl acetate; ethers such as tetrahydrofuran, dioxane, diethyl ether, dimethoxyethane, or tert-butyl methyl ether; dimethylformamide; and mixed solvents thereof. Preferred solvents are water and alcohols.

Acids such as hydriodic acid and/or catalysts such as a phase-transfer catalyst can be added to a reaction system in which the above reaction is carried out.

Examples of a phase-transfer catalyst may include a quaternary ammonium salt, a phosphonium salt, and a pyridinium salt.

Examples of a quaternary ammonium salt may include quaternary ammonium salts, wherein a group selected from the following group is substituted: a linear or branched alkyl group containing 1 to 18 carbon atoms; a phenylalkyl group wherein the alkyl portion is a linear or branched alkyl group containing 1 to 6 carbon atoms; and a phenyl group. Specific examples of such a quaternary ammonium salt may include tetrabutylammonium chloride, tetrabutylammonium bromide, tetrabutylammonium fluoride, tetrabutylammonium iodide, tetrabutylammonium hydroxide, tetrabutylammonium bisulfite, tributylmethylammonium chloride, tributylbenzylammonium chloride, tetrapentylammonium chloride, tetrapentylammonium bromide, tetrahexylammonium chloride, benzyldimethyloctylammonium chloride, methyltrihexylammonium chloride, benzyldimethyloctadecanylammonium chloride, methyltridecanylammonium chloride, benzyltripropylammonium chloride, benzyltriethylammonium chloride, phenyltriethylammonium chloride, tetraethylammonium chloride, and tetramethylammonium chloride.

Examples of a phosphonium salt may include phosphonium salts wherein a linear or branched alkyl group containing 1 to 18 carbon atoms is substituted. A specific example of such a phosphonium salt may be tetrabutylphosphonium chloride.

Examples of a pyridinium salt may include pyridinium salts wherein a linear or branched alkyl group containing 1 to 18 carbon atoms is substituted. A specific example of such a pyridinium salt may be 1-dodecanylpyridinium chloride.

The aforementioned phase-transfer catalyst is used singly or in combination of two or more types.

The phase-transfer catalyst is used, to 1 mole of the compound (2), at an amount generally between 0.01 and 1 mole, and preferably between 0.01 and 0.5 moles.

The above reaction is carried out at a temperature generally between 0° C. and 150° C., and preferably between 0° C. and 120° C., and it is generally carried out for 1 to 80 hours before termination.

In the above reaction, a chlorine atom or bromine atom at position 5 of the imidazole ring is selectively iodinated, and thus, the compound (3) is efficiently produced.

The reaction to obtain the compound (1) from the compound (3) is carried out in an appropriate solvent in the presence of a reducing agent.

Known hydrogenation reducing agents, catalytic hydrogenation reducing agents, and other agents are used as such reducing agents.

Examples of a hydrogenation reducing agent may include: sulfite compounds such as sodium bisulfite, sodium sulfite, sodium pyrosulfite, ammonium sulfite, ammonium sulfite monohydrate, or ammonium bisulfite; tetra lower alkyl ammonium borohydrides such as tetra methyl ammonium borohydride, tetra ethyl ammonium borohydride, tetra-n-butyl ammonium borohydride, or tetra-n-butyl ammonium cyanoborohydride; sodium cyanoborohydride, lithium cyanoborohydride, sodium borohydride, and diborane. These hydrogenation reducing agents are used singly or in combination of two or more types.

Examples of a catalytic hydrogenation reducing agent may include palladium, palladium-black, palladium-carbon, palladium hydroxide-carbon, rhodium-alumina, platinum, platinum oxide, copper chromite, palladium acetate, platinum-alumina, platinum-carbon, palladium-alumina, platinum black, and Raney nickel. These catalytic hydrogenation reducing agents are used singly or in combination of two or more types.

Of these reducing agents, catalytic hydrogenation reducing agents, in particular, platinum oxide and palladium-alumina are preferable.

In the present invention, the aforementioned hydrogenation reducing agents and catalytic hydrogenation reducing agents can be used in combination.

Examples of a solvent used herein may include water; fatty acids such as acetic acid; lower alcohols such as methanol, ethanol, or isopropanol; aliphatic hydrocarbons such as n-hexane or cyclohexane; ketones such as acetone or methyl ethyl ketone; ethers such as diethyl ether, tetrahydrofuran, diisopropyl ether, monoglime, diglime, 1,4-dioxane, or dimethoxyethane; aromatic hydrocarbons such as benzene, toluene, or xylene; esters such as ethyl acetate, methyl acetate, or n-butyl acetate; aprotic polar solvents such as dimethyl sulfoxide, N,N-dimethylformamide, N,N-dimethylacetamide, or 1-methyl-2-pyrrolidinone (NMP); and their mixed solvents.

When diborane or the like is used as a hydrogenation reducing agent, it is adequate to use an anhydrous solvent. When platinum oxide or palladium-alumina is used as a catalytic hydrogenation reducing agent, it is preferable to use mixed solvents containing water, in particular, mixed solvents consisting of water, and fatty acids, ketones, ethers, or aprotic polar solvents.

A hydrogenation reducing agent is used to 1 mole of the compound (3) at an amount of generally at least 1 mole, and preferably between 1 and 10 moles.

The reaction in which a hydrogenation reducing agent is used is carried out at a temperature generally between 0° C. and 150° C., and preferably between 0° C. and 120° C. The reaction is generally carried out for 1 to 30 hours before termination.

When a catalytic hydrogenation reducing agent is used, the reaction is carried out in a hydrogen atmosphere under generally between normal pressure and 20 atmospheres, and preferably between normal pressure and 10 atmospheres, at a temperature generally between −30° C. and 100° C., and preferably between 0° C. and 80° C. The reaction is generally carried out for 1 to 90 hours before termination.

A catalytic hydrogenation reducing agent is used to the compound (3) at a weight ratio generally between 0.1% by weight and 40% by weight, and preferably between 0.1% by weight and 20% by weight.

In order to promote the reaction, amines such as trimethylamine, triethylamine, or N-ethyldiisopropylamine may be added to the reaction system in which a catalytic hydrogenation reducing agent is used.

As a result of the aforementioned reduction reaction, an iodine atom substituted for position 5 of the imidazole ring is selectively eliminated, so that a desired compound represented by general formula (1) can efficiently be obtained. The present inventors have found such a fact for the first time.

The 4-nitroimidazole compound represented by general formula (1) of the present invention can be induced to a compound (13a) or (13b) that is useful as an antitubercular agent, for example, by the methods represented by the following Reaction scheme-4 and Reaction scheme-5:

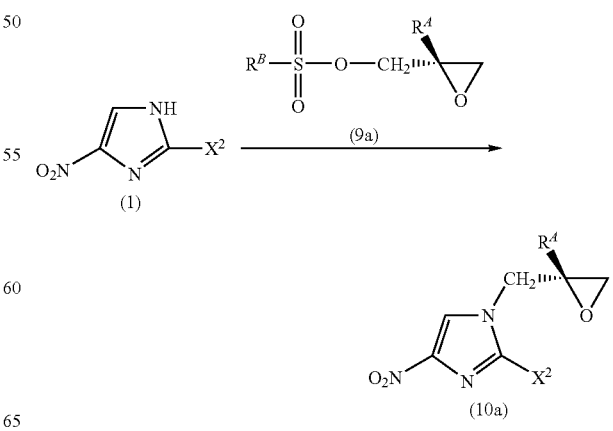

Reaction scheme-4

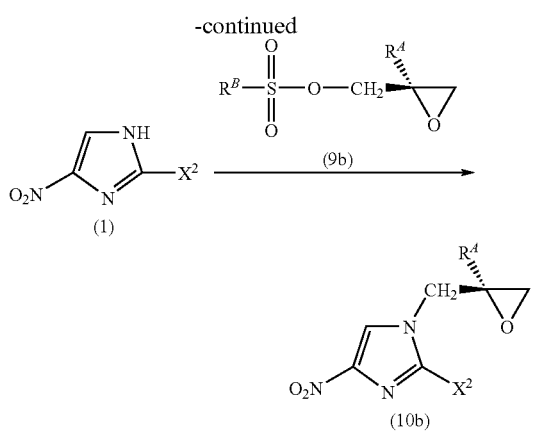

wherein $X^2$ is the same as defined above; $R^A$ represents a hydrogen atom or lower alkyl group; and $R^B$ represents the following group:

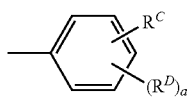

wherein $R^C$ represents a nitro group; $R^D$ represents a halogen atom or lower alkyl group; and a represents 0, 1, or 2, and when a represents 2, two $R^D$ may be either identical or different.

The reaction between the 4-nitroimidazole compound represented by general formula (1) and the compound (9a) or (9b) is carried out in a suitable solvent in the presence of a basic compound.

Examples of a solvent used herein may include: aromatic hydrocarbons such as benzene, toluene, or xylene; ethers such as diethyl ether, tetrahydrofuran, dixane, or diethylene glycol dimethyl ether; halogenated hydrocarbons such as dichloromethane, chloroform, or carbon tetrachloride; lower alcohols such as methanol, ethanol, isopropanol, butanol, or tert-butanol; acetic acid; esters such as ethyl acetate or methyl acetate; ketones such as acetone or methyl ethyl ketone; acetonitrile; pyridine; 2,4,6-coluidine; dimethyl sulfoxide; dimethylformamide; hexamethyl phosphoric triamide; and their mixed solvents.

Known inorganic bases and organic bases can widely be used as basic compounds.

Examples of an inorganic base may include: alkali metal carbonates such as sodium carbonate or potassium carbonate; alkali metal hydrogencarbonates such as sodium bicarbonate or potassium bicarbonate; alkali metal hydroxides such as sodium hydroxide or potassium hydroxide; alkali metal phosphates such as sodium phosphate or potassium phosphate; alkali metal hydrides such as sodium hydride or potassium hydride; alkali metals such as potassium or sodium; alkali metal amidates such as sodium amide; and alkali metal alcoholates such as sodium methylate or sodium ethylate.

Examples of an organic base may include pyridine, trimethylamine, triethylamine, N-ethyldiisopropylamine, 2,4,6-coluidine, dimethyl aniline, dimethylaminopyridine, 1-methyl-2-pyrrolidinone (NMP), N-methylmorpholine, N,N-dimethyl-4-aminopyridine, 1,5-diazabicyclo[4.3.0]nonen-5 (DBN), 1,8-diazabicyclo[5.4.0]undecen-7 (DBU), and 1,4-diazabicyclo[2.2.2]octan (DABCO).

These basic compounds are used singly or in combination of two or more types.

The compound (1) is used to 1 mole of the compound (9a) or (9b) at an amount of generally at least 1 mole, and preferably between 1 and 3 moles. The basic compound is used to 1 mole of the compound (9a) or (9b) at an amount generally between 1 and 10 moles, and preferably between equimolar and 5 moles.

The reaction between the compound (1) and the compound (9a) or (9b) is generally carried out at a temperature generally between room temperature and 150° C., and preferably between room temperature and 100° C. The reaction is generally carried out for 1 to 100 hours before termination.

During the above reaction, halides such as cesium fluoride may be added to the reaction system.

Reaction scheme-5

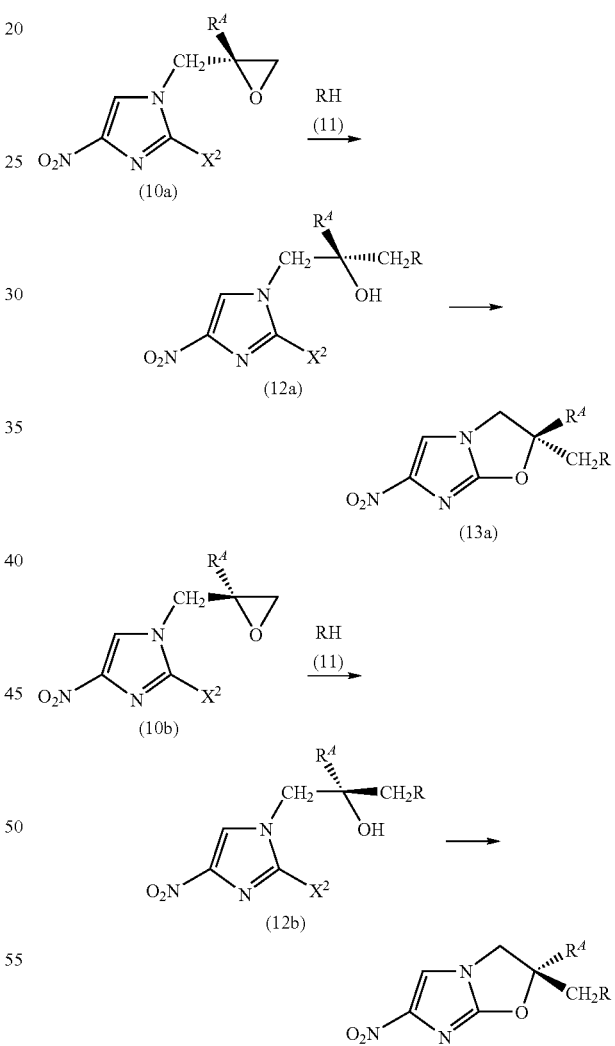

wherein $R^A$ and $X^2$ are the same as defined above; and R represents a group represented by the following general formula (A), (B), (C), (D), (E), (F), or (G)

A group represented by general formula (A):

—OR$^3$ (A)

(wherein R³ represents:
A1) a hydrogen atom;
A2) a C1-C6 alkyl group;
A3) a C1-C6 alkoxy-C1-C6 alkyl group;
A4) a phenyl C1-C6 alkyl group (wherein, on the phenyl ring, at least one selected from the following group may be substituted: a phenyl C1-C6 alkoxy group; a halogen substituted or unsubstituted C1-C6 alkyl group; and a halogen substituted or unsubstituted C1-C6 alkoxy group; and a phenoxy group [wherein, on the phenyl ring, at least one halogen substituted or unsubstituted C1-C6 alkoxy group may be substituted]);
A5) a biphenylyl C1-C6 alkyl group;
A6) a phenyl C2-C6 alkenyl group;
A7) a C1-C6 alkylsulfonyl group;
A8) a benzenesulfonyl group wherein a C1-C6 alkyl group may be substituted;
A9) a C1-C6 alkanoyl group;
A10) a group represented by general formula (Aa):

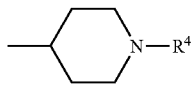

(Aa)

(wherein R⁴ represents: a C1-C6 alkoxycarbonyl group; a phenyl C1-C6 alkoxycarbonyl group [wherein, on the phenyl ring, at least one selected from the group consisting of a phenyl C1-C6 alkoxy group, a halogen substituted or unsubstituted C1-C6 alkyl group, and a halogen substituted or unsubstituted C1-C6 alkoxy group, may be substituted]; or a phenyl C1-C6 alkyl group [wherein, on the phenyl ring, at least one selected from the group consisting of a phenyl C1-C6 alkoxy group, a halogen substituted or unsubstituted C1-C6 alkyl group, and a halogen substituted or unsubstituted C1-C6 alkoxy group, may be substituted]);
A11) a biphenylyl C1-C6 alkoxycarbonyl group;
A12) a benzoxazolyl C1-C6 alkyl group (wherein, on the benzoxazole ring, at least one oxo group may be substituted);
A13) a benzoxazolyl group; or
A14) an oxazolyl C1-C6 alkyl group (wherein, on the oxazole ring, at least one selected from the group consisting of a phenyl group and a C1-C6 alkyl group may be substituted).
A group represented by general formula (B):

—SR⁵ (B)

(wherein R⁵ represents a tetrazolyl group [wherein, on the tetrazole ring, a C1-C6 alkyl group or a phenyl group which may have a halogen atom may be substituted] or a benzoxazolyl group).
A group represented by general formula (C):

—COOR⁶ (C)

(wherein R⁶ represents a C1-C6 alkyl group).
A carbamoyloxy group represented by general formula (D):

—OOCNR⁷R⁸ (D)

(wherein R⁷ and R⁸ each identically or differently represent:
D1) a hydrogen atom;
D2) a C1-C8 alkyl group;
D3) a halogen substituted C1-C6 alkyl group;
D4) a C1-C6 alkoxycarbonyl-C1-C6 alkyl group;
D5) a C3-C8 cycloalkyl group;
D6) a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);
D7) a phenyl group (wherein, on the phenyl ring, 1 to 3 groups selected from the group consisting of a halogen atom, a halogen substituted or unsubstituted C1-C6 alkyl group, a halogen substituted or unsubstituted C1-C6 alkoxy group, a C1-C6 alkanoyl group, a carboxyl group, a C1-C6 alkoxycarbonyl group, a phenyl C1-C6 alkoxycarbonyl group, a carbamoyl group, a C1-C6 alkylcarbamoyl group, an aminosulfonyl group, and a morpholino group, may be substituted);
D8) a naphthyl group; or
D9) a pyridyl group; or further,
D10) R⁷ and R⁸ may bind to each other together with nitrogen atoms adjacent thereto directly or through other heteroatoms or carbon atoms, so as to form a saturated heterocyclic group represented by any one of
(D10-1) to (D10-3) indicated below or a benzene condensed heterocylic group represented by any one of
(D10-4) to (D10-7) indicated below:
(D10-1) a piperazinyl group represented by general formula (Da):

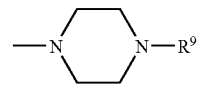

(Da)

(wherein R⁹ represents:
(Da1) a hydrogen atom;
(Da2) a C1-C6 alkyl group;
(Da3) a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);
(Da4) a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);
(Da5) a C1-C6 alkoxycarbonyl group;
(Da6) a phenyl C1-C6 alkoxycarbonyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);
(Da7) a phenyl C3-C6 alkenyloxycarbonyl group (wherein, on the phenyl ring, at least one halogen substituted or unsubstituted C1-C6 alkyl group may be substituted); or
(Da8) a phenyl C1-C6 alkylidene substituted amino group (wherein, on the phenyl ring, at least one halogen substituted or unsubstituted C1-C6 alkyl group may be substituted));

(D10-2) a group represented by general formula (Db):

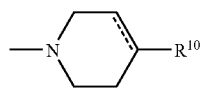

(Db)

(wherein the dotted line represents that the bond may be a double bond; and $R^{10}$ represents:
(Db1) a hydrogen atom;
(Db2) a phenyl group (wherein, on the phenyl ring, at least one selected from the group consisting of halogen, a halogen substituted or unsubstituted C1-C6 alkyl group, and a halogen substituted or unsubstituted C1-C6 alkoxy group, may be substituted);
(Db3) a phenoxy group (wherein, on the phenyl ring, at least one halogen substituted or unsubstituted C1-C6 alkyl group may be substituted); or
(Db4) a phenylamino group (wherein, on the phenyl ring, at least one halogen substituted or unsubstituted C1-C6 alkyl group may be substituted));
(D10-3) a morpholino group;
(D10-4) an indolinyl group (wherein, on the indoline ring, at least one halogen atom may be substituted);
(D10-5) an isoindolinyl group (wherein, on the isoindoline ring, at least one halogen atom may be substituted);
(D10-6) a 1,2,3,4-tetrahydroquinolyl group (wherein, on the 1,2,3,4-tetrahydroquinoline ring, at least one halogen atom may be substituted); or
(D10-7) a 1,2,3,4-tetrahydroisoquinolinyl group (wherein, on the 1,2,3,4-tetrahydroisoquinoline ring, at least one halogen atom may be substituted).

A phenoxy group represented by general formula (E):

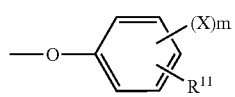

(E)

[wherein X represents a halogen atom or an amino substituted C1-C6 alkyl group which may have a C1-C6 alkyl group as a substituent; m represents an integer between 0 and 3; and $R^{11}$ represents:
E1) a hydrogen atom;
E2) a halogen substituted or unsubstituted C1-C6 alkyl group;
E3) a halogen substituted or unsubstituted C1-C6 alkoxy group;
E4) a group represented by general formula (Ea):

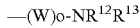

—(W)o-NR$^{12}$R$^{13}$ (Ea)

(wherein W represents the group —CO— or a C1-C6 alkylene group; o represents 0 or 1; and $R^{12}$ and $R^{13}$ each identically or differently represent:
(Ea1) a hydrogen atom;
(Ea2) a C1-C6 alkyl group;
(Ea3) a C1-C6 alkanoyl group;
(Ea4) a C1-C6 alkoxycarbonyl group;
(Ea5) a phenyl C1-C6 alkyl group (wherein, on the phenyl ring, at least one selected from the following group may be substituted: a halogen atom; a halogen substituted or unsubstituted C1-C6 alkyl group; a halogen substituted or unsubstituted C1-C6 alkoxy group; and a phenoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], and further wherein, a C1-C6 alkoxyimino group may be substituted for a C1-C6 alkyl portion thereof);
(Ea6) a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);
(Ea7) a benzoyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);
(Ea8) a pyridyl group (wherein, on the pyridine ring, at least one halogen atom may be substituted);
(Ea9) a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);
(Ea10) a phenoxy C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); or
(Ea11) a benzoyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted));
E5) an imidazolyl group;
E6) a triazolyl group;
E7) a morpholino group;
E8) a thiomorpholino group;
E9) an s-oxide thiomorpholino group;
E10) a piperidyl group represented by general formula (Eaa):

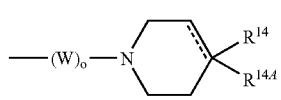

(Eaa)

(wherein W and o are the same as defined above; $R^{14A}$ represents a hydrogen atom, a hydroxyl group, a C1-C6 alkoxy group, or a phenyl group [wherein, on the phenyl ring, a halogen atom may be substituted]; the dotted line represents that the bond may be a double bond, and when the dotted line represents such a double bond, only $R^{14}$ is substituted; and $R^{14}$ and $R^{14A}$ may bind to each other together with carbon atoms adjacent thereto, so as to form a C1-C4 alkylenedioxy group, wherein $R^{14}$ represents:
(Eaa1) a hydrogen atom;
(Eaa2) a C1-C6 alkoxycarbonyl group;
(Eaa3) a phenoxy group (wherein, on the phenyl ring, at least one selected from the following group may be substituted: a halogen atom; a halogen substituted or unsubstituted C1-C6 alkyl group; a halogen substituted or unsubstituted C1-C6 alkoxy group; a C1-C4 alkylenedioxy group; a C1-C6 alkoxycarbonyl group; a cyano group; a C2-C6 alkenyl group; a nitro group; a phenyl group; an amino group which may have, as a substituent, a group selected from the group consisting of a phenyl group, a C1-C6 alkyl group, a carbamoyl group, and a C1-C6 alkanoyl group; a C1-C6 alkanoyl substituted C1-C6 alkyl group; a hydroxyl group; a C1-C6 alkoxycarbonyl substituted C1-C6 alkyl group; a phenyl C1-C6 alkyl group; a C1-C6 alkanoyl group; a C1-C6 alkylthio group; a 1,2,4-triazolyl group; an isoxazolyl group; an imidazolyl group; a benzothiazolyl group; a 2H-benzotriazolyl group; a pyrrolyl group; a benzoxazolyl group; a piperazinyl group [wherein, on the piperazine ring, at least one selected from the group consisting of a C1-C6 alkoxycarbonyl group and a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) may be substituted as a substituent]; a piperidyl group [wherein, on the piperidine ring, at least one amino group may be substituted, wherein, on the amino group, at least one selected from the group consisting of a C1-C6 alkyl group and a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) may be substituted as a substituent]; and a carbamoyl group);

(Eaa4) a hydroxyl group;

(Eaa5) a carboxy group;

(Eaa6) a phenyl group (wherein, on the phenyl ring, at least one selected from the group consisting of a phenoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted as a substituent], a halogen atom, a halogen substituted or unsubstituted C1-C6 alkyl group, and a halogen substituted or unsubstituted C1-C6 alkoxy group, may be substituted as a substituent);

(Eaa7) a C1-C6 alkoxy group;

(Eaa8) a C3-C8 cycloalkyl-C1-C6 alkoxy group;

(Eaa9) a phenylcarbamoyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

(Eaa10) a tetrahydropyranyloxy group;

(Eaa11) a 1,3-dioxolanyl group;

(Eaa12) an oxo group;

(Eaa13) a naphthyloxy group (wherein, on the naphthalene ring, at least one C1-C6 alkyl group may be substituted);

(Eaa14) a 2,3-dihydrobenzofuryloxy group (wherein, on the 2,3-dihydrobenzofuran ring, at least one selected from the group consisting of a C1-C6 alkyl group and an oxo group may be substituted);

(Eaa15) a benzothiazolyloxy group (wherein, on the benzothiazole ring, at least one C1-C6 alkyl group may be substituted);

(Eaa16) a 1,2,3,4-tetrahydronaphthyloxy group (wherein, on the 1,2,3,4-tetrahydronaphthalene ring, at least one oxo group may be substituted);

(Eaa17) a 1,3-benzoxathiolanyloxy group (wherein, on the 1,3-benzoxathiolane ring, at least one oxo group may be substituted);

(Eaa18) an isoquinolyloxy group;

(Eaa19) a pyridyloxy group;

(Eaa20) a quinolyloxy group (wherein, on the quinoline ring, at least one C1-C6 alkyl group may be substituted);

(Eaa21) a dibenzofuryloxy group;

(Eaa22) a 2H-chromenyloxy group (wherein, on the 2H-chromene ring, at least one oxo group may be substituted);

(Eaa23) a benzoisoxazolyloxy group;

(Eaa24) a quinoxalyloxy group;

(Eaa25) a 2,3-dihydro-1H-indenyloxy group (wherein, on the 2,3-dihydro-1H-indene ring, at least one oxo group may be substituted);

(Eaa26) a benzofurazanyloxy group; or (Eaa27) a phenyl C2-C6 alkenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted));

E11) a group represented by general formula (Eab):

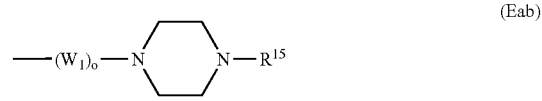

(Eab)

(wherein o is the same as defined above; $W_1$ represents a lower alkylene group; and $R^{15}$ represents:

(Eab1) a hydrogen atom;

(Eab2) a C1-C6 alkyl group (wherein, on the alkyl group, a morpholino group, a benzoyl group, a carbamoyl group which may have a C1-C6 alkyl group as a substituent, or a cyano group may be substituted);

(Eab3) a C3-C8 cycloalkyl group;

(Eab4) a phenyl C1-C6 alkyl group (wherein, on the phenyl ring, at least one selected from the group consisting of a halogen atom, a cyano group, a phenyl group, a nitro group, a C1-C6 alkylthio group, a C1-C6 alkylsulfonyl group, a phenyl C1-C6 alkoxy group, a C2-C6 alkanoyloxy group, a halogen substituted or unsubstituted C1-C6 alkyl group, a halogen substituted or unsubstituted C1-C6 alkoxy group, and a 1,2,3-thiadiazole group, may be substituted);

(Eab5) a C2-C6 alkenyl group;

(Eab6) a phenyl group (wherein, on the phenyl ring, at least one selected from the group consisting of a halogen atom, a cyano group, a halogen substituted or unsubstituted C1-C6 alkyl group, and a halogen substituted or unsubstituted C1-C6 alkoxy group, may be substituted);

(Eab7) a C1-C6 alkanoyl group;

(Eab8) a phenyl C2-C6 alkanoyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

(Eab9) a benzoyl group (wherein, on the benzene ring, at least one selected from the group consisting of a halogen atom, a halogen substituted or unsubstituted C1-C6 alkyl group, and a halogen substituted or unsubstituted C1-C6 alkoxy group, may be substituted);

(Eab10) a C1-C20 alkoxycarbonyl group (wherein, on the alkoxy group, at least one selected from the group consisting of a halogen atom, an amino group which may have a C1-C6 alkyl group as a substituent, and a C1-C6 alkoxy substituted C1-C6 alkoxy group, may be substituted);

(Eab11) a phenyl C1-C6 alkoxycarbonyl group (wherein, on the phenyl ring, at least one selected from the group consisting of a halogen atom, a halogen substituted or unsubstituted C1-C6 alkyl group, a halogen substituted or unsubstituted C1-C6 alkoxy group, a nitro group, a halogen substituted or unsubstituted C1-C6 alkylthio group, an amino group which may have a C1-C6 alkanoyl group, a phenyl C1-C6 alkoxy group, a C1-C6 alkoxycarbonyl group, and a 1,2,3-thiadiazolyl group, may be substituted);

(Eab12) a phenyl C3-C6 alkenyloxycarbonyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

(Eab13) a phenoxycarbonyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

(Eab14) a phenyl C1-C6 alkylcarbamoyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

(Eab15) a phenylcarbamoyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

(Eab16) a benzofuryl substituted C1-C6 alkoxycarbonyl group (wherein, on the benzofuran ring, at least one halogen atom may be substituted);

(Eab17) a benzothienyl C1-C6 alkoxycarbonyl group (wherein, on the benzothiophene ring, at least one selected from the group consisting of a halogen atom and a halogen substituted or unsubstituted C1-C6 alkoxy group may be substituted);

(Eab18) a naphthyl substituted C1-C6 alkoxycarbonyl group;

(Eab19) a pyridyl substituted C1-C6 alkoxycarbonyl group (wherein, on the pyridine ring, at least one halogen atom may be substituted);

(Eab20) a furyl substituted C1-C6 alkoxycarbonyl group (wherein, on the furan ring, at least one nitro group may be substituted);

(Eab21) a thienyl substituted C1-C6 alkoxycarbonyl group (wherein, on the thiophene ring, at least one halogen atom may be substituted);

(Eab22) a thiazolyl substituted C1-C6 alkoxycarbonyl group (wherein, on the thiazole ring, at least one selected from the group consisting of a C1-C6 alkyl group and a phenyl group [wherein, on the phenyl ring, at least one halogen substituted or unsubstituted C1-C6 alkyl group may be substituted] may be substituted);

(Eab23) a tetrazolyl substituted C1-C6 alkoxycarbonyl group (wherein, on the tetrazole ring, at least one selected from the group consisting of a C1-C6 alkyl group and a phenyl group [wherein, on the phenyl ring, at least one halogen atom may be substituted] may be substituted);

(Eab24) a 2,3-dihydro-1H-indenyloxycarbonyl group;

(Eab25) an adamantane substituted C1-C6 alkoxycarbonyl group;

(Eab26) a phenyl C3-C6 alkynyloxycarbonyl group;

(Eab27) a phenylthio C1-C6 alkoxycarbonyl group;

(Eab28) a phenyl C1-C6 alkoxy substituted C1-C6 alkoxycarbonyl group;

(Eab29) a C2-C6 alkenyloxycarbonyl group;

(Eab30) a C2-C6 alkynyloxycarbonyl group;

(Eab31) a C3-C8 cycloalkyl substituted C1-C6 alkoxycarbonyl group; or (Eab32) a benzoyl substituted C1-C6 alkoxycarbonyl group);

E12) a group represented by general formula (Eb):

(Eb)

(wherein the dotted line represents that the bond may be a double bond; and $R^{16}$ represents the same group as $R^{15}$);

E13) a group represented by general formula (Ec):

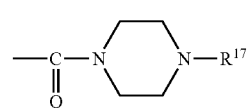

(Ec)

(wherein $R^{17}$ represents:

(Ec1) a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

(Ec2) a C1-C6 alkoxycarbonyl group; or (Ec3) a phenyl C1-C6 alkoxycarbonyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted));

E14) a pyridyl group;

E15) a group represented by general formula (Ee):

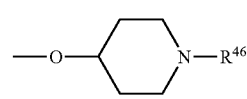

(Ee)

(wherein $R^{46}$ represents: a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a phenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a phenyl C1-C6 alkoxycarbonyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; or a C1-C6 alkoxycarbonyl group);

E16) a phenoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

E17) a benzoyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

E18) a 8-azabicyclo[3,2,1]octyl group (wherein, on the 8-azabicyclo[3,2,1]octane ring, at least one phenoxy group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted));

E19) a group represented by the following general formula (Ef):

—CH=N—NR$^{47}$R$^{48}$  (Ef)

(wherein R$^{47}$ and R$^{48}$ each identically or differently represent: a hydrogen atom; a C1-C6 alkyl group; a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; or a pyridyl group [wherein, on the pyridine ring, at least one halogen substituted or unsubstituted C1-C6 alkyl group may be substituted as a substituent], and further wherein R$^{47}$ and R$^{48}$ may bind to each other together with nitrogen atoms adjacent thereto directly or through other heteroatoms, so as to form a 5-7 membered saturated heterocyclic ring, wherein, on the heterocyclic ring, at least one phenyl group may be substituted as a substituent [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]);

E20) a phenyl C1-C6 alkoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

E21) an amino substituted C2-C6 alkenyl group (wherein, on the amino group, at least one selected from the group consisting of a C1-C6 alkyl group and a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted] may be substituted); or E22) an oxazolidinyl group (wherein, on the oxazolidine ring, at least one oxo group may be substituted)].

A group represented by general formula (F):

—NR$^{19}$R$^{20}$  (F)

[wherein R$^{19}$ and R$^{20}$ each identically or differently represent:

F1) a hydrogen atom;

F2) a C1-C6 alkyl group;

F3) a phenyl C1-C6 alkyl group (wherein, on the phenyl ring, at least one selected from the following group may be substituted: a phenoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a halogen atom; a halogen substituted or unsubstituted C1-C6 alkyl group; a halogen substituted or unsubstituted C1-C6 alkoxy group; an amino group (wherein, on the amino group, at least one selected from the group consisting of a C1-C6 alkyl group and a phenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted] may be substituted); a piperazinyl group [wherein, on the piperazine ring, at least one phenyl C1-C6 alkyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)]; and a piperidyl group [wherein, on the piperidine ring, at least one amino group may be substituted, wherein on the amino group, at least one selected from the group consisting of a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) and a C1-C6 alkyl group may be substituted]);

F4) a phenoxy C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

F5) an amino C1-C6 alkyl group (wherein, on the amino group, at least one selected from the group consisting of a C1-C6 alkyl group, a C1-C6 alkoxycarbonyl group, and a phenyl group [wherein, on the phenyl ring, at least one selected from the group consisting of a halogen atom and a halogen substituted or unsubstituted C1-C6 alkyl group may be substituted], may be substituted);

F6) a phenyl group (wherein, on the phenyl ring, at least one selected from the group consisting of a halogen atom, a phenoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], and a C1-C6 alkoxycarbonyl group, may be substituted);

F7) a C1-C6 alkoxycarbonyl group;

F8) a phenyl C1-C6 alkoxycarbonyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

F9) a group represented by general formula (Fa):

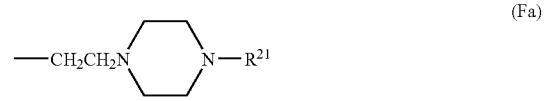

—CH$_2$CH$_2$N⟨ ⟩N—R$^{21}$   (Fa)

(wherein R$^{21}$ represents: a C1-C6 alkoxycarbonyl group; a phenyl C1-C6 alkoxycarbonyl group (wherein, on the phenyl ring, at least one selected from the group consisting of a halogen atom, a cyano group, a halogen substituted or unsubstituted C1-C6 alkyl group, and a halogen substituted or unsubstituted C1-C6 alkoxy group, may be substituted); a phenyl C1-C6 alkyl group (wherein, on the phenyl ring, at least one selected from the group consisting of a halogen atom and a halogen substituted or unsubstituted C1-C6 alkyl group may be substituted); or a phenyl group (wherein, on the phenyl ring, at least one selected from the group consisting of a halogen atom, a cyano group, a halogen substituted or unsubstituted C1-C6 alkyl group, and a halogen substituted or unsubstituted C1-C6 alkoxy group, may be substituted));

F10) a 1-substituted-4-piperidyl group represented by general formula (Fb):

$$\text{—}\underset{}{\bigcirc}\text{N—R}^{22} \qquad (Fb)$$

(wherein $R^{22}$ represents: a C1-C6 alkoxycarbonyl group; a phenyl C1-C6 alkoxycarbonyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); or a phenyl group (wherein, on the phenyl ring, at least one selected from the group consisting of a halogen atom, a cyano group, a halogen substituted or unsubstituted C1-C6 alkyl group, and a halogen substituted or unsubstituted C1-C6 alkoxy group, may be substituted)); or F11) a piperidyl C1-C6 alkyl group (wherein, on the piperidine ring, at least one phenoxy group may be substituted (wherein, on the phenyl ring, at least one halogen substituted or unsubstituted C1-C6 alkyl group may be substituted)); or further, F12) $R^{19}$ and $R^{20}$ may bind to each other together with nitrogen atoms adjacent thereto directly or through other heteroatoms or carbon atoms, so as to form a heterocyclic ring represented by any one of (F12-1) to (F12-10) indicated below:

(F12-1) a group represented by general formula (Fc):

$$\text{—N}\underset{}{\bigcirc}\text{R}^{23} \qquad (Fc)$$

[wherein the dotted line represents that the bond may be a double bond; and $R^{23}$ represents:

(Fc1) a C1-C6 alkyl group;
(Fc2) a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);
(Fc3) a phenyl group (wherein, on the phenyl ring, at least one selected from the following group may be substituted: a halogen atom; a halogen substituted or unsubstituted C1-C6 alkyl group; a halogen substituted or unsubstituted C1-C6 alkoxy group; an amino group which may have, as a substituent, a group selected from the group consisting of a C1-C6 alkyl group and a phenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a phenoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a phenyl C1-C6 alkoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; and a piperidyl group [wherein, on the piperidine ring, at least one amino group may be substituted, and wherein, on the amino group, at least one selected from the group consisting of a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) and a C1-C6 alkyl group may be substituted])

(Fc4) a phenyl C1-C6 alkoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);
(Fc5) a biphenylyl C1-C6 alkoxy group;
(Fc6) a phenyl C3-C6 alkenyloxy group wherein, on the phenyl ring, at least one halogen atom may be substituted;
(Fc7) a phenoxy group (wherein, on the phenyl ring, at least one selected from the group consisting of a halogen atom, a cyano group, a halogen substituted or unsubstituted C1-C6 alkyl group, and a halogen substituted or unsubstituted C1-C6 alkoxy group, may be substituted);
(Fc8) a benzoyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);
(Fc9) a C1-C6 alkoxycarbonyl group;
(Fc10) a phenyl C1-C6 alkoxycarbonyl group (wherein, on the phenyl ring, at least one halogen substituted or unsubstituted C1-C6 alkoxy group may be substituted);
(Fc11) a phenyl C1-C6 alkylcarbamoyl group wherein, on the phenyl ring, at least one halogen atom may be substituted;
(Fc12) a phenylcarbamoyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);
(Fc13) a phenylthio group (wherein, on the phenyl ring, at least one halogen substituted or unsubstituted C1-C6 alkoxy group may be substituted);
(Fc14) a phenyl sulfoxide (wherein, on the phenyl ring, at least one halogen substituted or unsubstituted C1-C6 alkoxy group may be substituted);
(Fc15) a pyridyl C1-C6 alkoxy group; or
(Fc16) a group represented by general formula (Fca):

$$\text{—(C=O)o-NR}^{24}\text{R}^{25} \qquad (Fca)$$

(wherein o is the same as defined above; $R^{24}$ and $R^{25}$ each represent:
(Fca1) a hydrogen atom;
(Fca2) a C1-C6 alkyl group;
(Fca3) a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);
(Fca4) a phenyl group (wherein, on the phenyl ring, at least one selected from the group consisting of a halogen atom, a cyano group, a halogen substituted or unsubstituted C1-C6 alkyl group, and a halogen substituted or unsubstituted C1-C6 alkoxy group, may be substituted);
(Fca5) a C1-C6 alkanoyl group;
(Fca6) a phenyl C2-C6 alkanoyl group wherein, on the phenyl ring, at least one halogen atom may be substituted;

(Fca7) a benzoyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

(Fca8) a C1-C6 alkoxycarbonyl group;

(Fca9) a phenyl C1-C6 alkoxycarbonyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

(Fca10) a phenylcarbamoyl group (wherein, on the phenyl ring, at least one halogen substituted or unsubstituted C1-C6 alkyl group may be substituted); or (Fca11) a piperidyloxycarbonyl group (wherein, on the piperidine ring, at least one phenyl group may be substituted as a substituent [wherein, on the phenyl ring, at least one halogen substituted or unsubstituted C1-C6 alkyl group may be substituted]); or further, (Fca12) $R^{24}$ and $R^{25}$ may form a 5- or 6-membered saturated heterocyclic ring via nitrogen atoms adjacent thereto, wherein, on the heterocyclic ring, at least one selected from the following group may be substituted: a C1-C6 alkoxycarbonyl group; a benzoyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); a phenoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); a phenyl C1-C6 alkoxycarbonyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); a phenyl C2-C6 alkenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); and a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

F12-2) a 4-substituted-1-piperazinyl group represented by general formula (Fd):

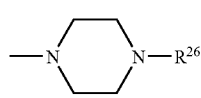

(Fd)

(wherein $R^{26}$ represents:

(Fd1) a hydrogen atom;

(Fd2) a C1-C6 alkyl group;

(Fd3) a C3-C8 cycloalkyl group;

(Fd4) a C3-C8 cycloalkyl C1-C6 alkyl group;

(Fd5) a C1-C6 alkoxycarbonyl C1-C6 alkyl group;

(Fd6) a phenyl C2-C6 alkenyl group;

(Fd7) a phenyl C1-C6 alkyl group (wherein, on the phenyl ring, 1 to 3 groups selected from the following group may be substituted: a halogen atom; a cyano group; a halogen substituted or unsubstituted C1-C6 alkyl group; a C3-C8 cycloalkyl group; a halogen substituted or unsubstituted C1-C6 alkoxy group; an amino group which may have a C1-C6 alkyl group as a substituent; a C1-C6 alkoxycarbonyl group; a phenoxy group; a phenyl C1-C6 alkyl group; a phenyl C2-C6 alkenyl group; a pyridyl group; an imidazolyl group; and a piperidyl group);

(Fd8) biphenylyl C1-C6 alkyl group (wherein, on the phenyl ring, at least one selected from the group consisting of a halogen atom, a halogen substituted or unsubstituted C1-C6 alkyl group, a halogen substituted or unsubstituted C1-C6 alkoxy group, and an amino group which may have a C1-C6 alkyl group as a substituent, may be substituted);

(Fd9) a naphthyl C1-C6 alkyl group;

(Fd10) a phenyl group (wherein, on the phenyl ring, at least one selected from the following group may be substituted: a halogen atom; a cyano group; an amino group which may have a C1-C6 alkyl group as a substituent; a halogen substituted or unsubstituted C1-C6 alkyl group; a halogen substituted or unsubstituted C1-C6 alkoxy group; a C1-C6 alkoxycarbonyl group; a carboxyl group; a phenoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; an amino C1-C6 alkyl group [wherein, on the amino group, at least one selected from the group consisting of a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) and a C1-C6 alkyl group may be substituted]; and a phenyl C1-C6 alkoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]);

(Fd11) a biphenylyl group (wherein, on the phenyl ring, at least one halogen substituted or unsubstituted C1-C6 alkyl group may be substituted);

(Fd12) an amino group, amino group wherein a C1-C6 alkoxycarbonyl group is substituted, phenyl C1-C6 alkylamino group (wherein, on the phenyl ring, at least one halogen substituted or unsubstituted C1-C6 alkyl group may be substituted), or phenylamino group (wherein, on the phenyl ring, at least one selected from the group consisting of a halogen atom and a halogen substituted or unsubstituted C1-C6 alkyl group may be substituted);

(Fd13) a benzoyl C1-C6 alkyl group (wherein, on the phenyl ring, at least one halogen atom may be substituted);

(Fd14) a phenylcarbamoyl C1-C6 alkyl group (wherein, on the phenyl ring, at least one halogen substituted or unsubstituted C1-C6 alkyl group may be substituted);

(Fd15) a thiazolyl C1-C6 alkyl group (wherein, on the thiazole ring, at least one selected from the group consisting of a halogen substituted or unsubstituted phenyl group and a C1-C6 alkyl group may be substituted);

(Fd16) an oxazolyl C1-C6 alkyl group (wherein, on the oxazole ring, at least one selected from the group consisting of a halogen substituted or unsubstituted phenyl group and a C1-C6 alkyl group may be substituted);

(Fd17) an indolyl C1-C6 alkyl group;
(Fd18) a furyl C1-C6 alkyl group (wherein, on the furan ring, at least one halogen substituted or unsubstituted phenyl group may be substituted);
(Fd19) an imidazolyl C1-C6 alkyl group (wherein, on the imidazole ring, a phenyl group may be substituted);
(Fd20) a quinolyl C1-C6 alkyl group;
(Fd21) a tetrazolyl group (wherein, on the tetrazole ring, a phenyl group may be substituted);
(Fd22) a pyrimidyl group wherein a phenyl group may be substituted;
(Fd23) a pyridyl group;
(Fd24) a benzoxazolyl group;
(Fd25) a benzothiazolyl group;
(Fd26) a benzoxazolyl C1-C6 alkyl group (wherein, on the benzoxazole ring, at least one oxo group may be substituted);
(Fd27) a phenoxy C2-C6 alkanoyl group wherein, on the phenyl ring, a halogen atom may be substituted;
(Fd28) a phenylthio C2-C6 alkanoyl group wherein, on the phenyl ring, a halogen atom may be substituted;
(Fd29) a phenyl C2-C6 alkanoyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);
(Fd30) a benzoyl group (wherein, on the phenyl ring, at least one selected from the group consisting of a halogen atom, a halogen substituted or unsubstituted C1-C6 alkyl group, a halogen substituted or unsubstituted C1-C6 alkoxy group, and an amino group which may have a C1-C6 alkyl group as a substituent, may be substituted);
(Fd31) a biphenylylcarbonyl group;
(Fd32) a pyridylcarbonyl group;
(Fd33) a phenyl C2-C6 alkenylcarbonyl group wherein, on the phenyl ring, a halogen atom may be substituted;
(Fd34) a phenyl C1-C6 alkylsulfonyl group wherein, on the phenyl ring, a halogen atom may be substituted;
(Fd35) a benzenesulfonyl group (wherein, on the benzene ring, at least one selected from the group consisting of a halogen atom and a C1-C6 alkyl group may be substituted);
(Fd36) a group represented by general formula (Fda):

—COOR$^{27}$           (Fda)

(wherein R27 represents:
(Fda1) a halogen substituted or unsubstituted C1-C8 alkyl group;
(Fda2) a C3-C8 cycloalkyl group;
(Fda3) a C3-C8 cycloalkyl-C1-C6 alkyl group;
(Fda4) a C1-C6 alkoxy-C1-C6 alkyl group;
(Fda5) an amino-C1-C6 alkyl group which may have a C1-C6 alkyl group;
(Fda6) a group represented by general formula (Fdb):

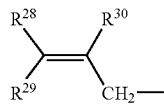
(Fdb)

(wherein each of R$^{28}$, R$^{29}$, and R$^{30}$ represents: a hydrogen atom; a C1-C6 alkyl group; or a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted));

(Fda7) a phenyl C1-C6 alkyl group (wherein, on the phenyl ring, 1 to 5 groups selected from the group consisting of a halogen atom, a halogen substituted or unsubstituted C1-C6 alkyl group, a halogen substituted or unsubstituted C1-C6 alkoxy group, a halogen substituted or unsubstituted C1-C6 alkylthio group, a phenyl C1-C6 alkoxy group, a hydroxy group, a C1-C6 alkylsulfinyl group, a C1-C6 alkylsulfonyl group, a C1-C6 alkylsulfonyloxy group, a cyano group, a C1-C6 alkanoyl group, a benzoyl group, a phenyl C1-C6 alkyl group which may have a C1-C6 alkoxy group at an alkyl portion thereof, an amino group, a nitro group, a carbamoyl group, a C1-C6 alkanoylamino group, a C1-C6 alkoxycarbonyl group, a C1-C6 alkylaminocarbonyl group, a C1-C6 alkoxycarbonylamino group, a tri C1-C6 alkylsiloxy group, a pyrrolyl group, a tetrahydropyranyloxy group, and an imidazolyl group, may be substituted);
(Fda8) a biphenylyl C1-C6 alkyl group;
(Fda9) a benzhydryl group (wherein, on the benzene ring, at least one selected from the group consisting of a halogen atom, a trifluoromethyl group, and a trifluoromethoxy group, may be substituted);
(Fda10) a phenoxy C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);
(Fda11) a phenyl C2-C6 alkynyl group (wherein, on the phenyl ring, at least one halogen substituted or unsubstituted C1-C6 alkyl group may be substituted);
(Fda12) a pyridyl C1-C6 alkyl group;
(Fda13) a group represented by general formula (Fdc):

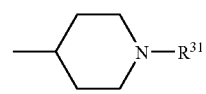
(Fdc)

(wherein R$^{31}$ represents: a phenyl group [wherein, on the phenyl ring, at least one selected from the group consisting of a halogen atom, a cyano group, a halogen substituted or unsubstituted C1-C6 alkyl group, and a halogen substituted or unsubstituted C1-C6 alkoxy group, may be substituted]; a phenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; or a benzoyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]);
(Fda14) a piperidino C1-C6 alkyl group (wherein, on the piperidine ring, a phenoxy group, which may have, as a substituent, at least one halogen substituted or unsubstituted alkyl group on the phenyl ring, may be substituted);
(Fda15) an amino C1-C6 alkyl group (wherein, on the amino group, at least one selected from the group consisting of a C1-C6 alkyl group and a phenyl group, which may have, as a substituent, a halogen substituted or unsubstituted C1-C6 alkoxy group on the phenyl ring, may be substituted);
(Fda16) a 1,2,3,6-tetrahydropyridyl C1-C6 alkyl group (wherein, on the 1,2,3,6-tetrahydropyridine ring, at least one phenyl group [wherein, on the phenyl ring, at least one halogen substituted or unsubstituted C1-C6 alkoxy group may be substituted]);

(Fda17) a naphthyl C1-C6 alkyl group;

(Fda18) a fluorenyl C1-C6 alkyl group;

(Fda19) a pyridyl C1-C6 alkyl group;

(Fda20) a furyl C1-C6 alkyl group (wherein, on the furan ring, a halogen substituted or unsubstituted phenyl group may be substituted);

(Fda21) a thienyl C1-C6 alkyl group;

(Fda22) an oxazolyl C1-C6 alkyl group (wherein, on the oxazole ring, a halogen atom or a halogen substituted or unsubstituted phenyl group may be substituted);

(Fda23) an oxadiazolyl C1-C6 alkyl group (wherein, on the oxadiazole ring, a halogen substituted or unsubstituted phenyl group may be substituted);

(Fda24) a pyrazolyl C1-C6 alkyl group (wherein, on the pyrazole ring, a halogen substituted or unsubstituted phenyl group may be substituted);

(Fda25) a benzothienyl C1-C6 alkyl group (wherein, on the benzothiophene ring, at least one selected from the group consisting of a halogen atom and a halogen substituted or unsubstituted C1-C6 alkoxy group may be substituted);

(Fda26) a thienyl C1-C6 alkyl group wherein, on the thiophene ring, a halogen atom may be substituted;

(Fda27) a benzothiazolyl C1-C6 alkyl group;

(Fda28) a benzofuryl C1-C6 alkyl group wherein, on the benzofuran ring, a halogen atom may be substituted;

(Fda29) an indolinyl C1-C6 alkyl group (wherein, on the indoline ring, at least one selected from the group consisting of a C1-C6 alkyl group and an oxo group may be substituted);

(Fda30) a benzoxazolyl C1-C6 alkyl group (wherein, on the benzoxazole ring, at least one selected from the group consisting of a halogen atom, a C1-C6 alkyl group, and an oxo group, may be substituted);

(Fda31) a chromenyl C1-C6 alkyl group;

(Fda32) a 1,2,3,4-tetrahydroquinolyl C1-C6 alkyl group (wherein, on the quinoline ring, at least one selected from the group consisting of a C1-C6 alkyl group and an oxo group may be substituted);

(Fda33) a thiazolyl C1-C6 alkyl group (wherein, on the thiazole ring, at least one selected from the group consisting of a halogen atom, a halogen substituted or unsubstituted phenyl group, and a C1-C6 alkyl group, may be substituted); or (Fda34) a tetrazolyl C1-C6 alkyl group (wherein, on the tetrazole ring, at least one selected from the group consisting of a halogen substituted or unsubstituted phenyl group and a C1-C6 alkyl group may be substituted);

(Fd37) a group represented by general formula (Fe):

(wherein Z represents —C=O or —C=S; $R^{32}$ and $R^{33}$ each identically or differently represent:

(Fe1) a hydrogen atom;

(Fe2) a C1-C6 alkyl group;

(Fe3) a C3-C8 cycloalkyl group;

(Fe4) a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

(Fe5) a phenyl C2-C6 alkenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); or (Fe6) a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); or further, (Fe7) $R^{32}$ and $R^{33}$ may bind to each other together with nitrogen atoms adjacent thereto through other carbon atoms, so as to form a piperidine ring or a 1,2,3,6-tetrahydropyridine ring, wherein, on the piperidine ring or the 1,2,3,6-tetrahydropyridine ring, a phenyl group may be substituted, and further, at least one selected from the group consisting of a halogen atom and a halogen substituted or unsubstituted C1-C6 alkyl group may be substituted on the phenyl group);

(Fd38) a group represented by general formula (Ff):

(wherein $R^{34}$ represents a hydrogen atom or C1-C6 lower alkyl group; and $R^{35}$ represents:

(Ff1) a C3-C8 cycloalkyl group;

(Ff2) a C3-C8 cycloalkenyl group;

(Ff3) a group represented by general formula (Ffa):

(wherein each of $R^{36}$, $R^{37}$, and $R^{38}$ represents: a hydrogen atom; a C1-C6 alkyl group; a phenyl group [wherein, on the phenyl ring, 1 to 5 groups selected from the group consisting of a halogen atom, a halogen substituted or unsubstituted C1-C6 alkyl group, a halogen substituted or unsubstituted C1-C6 alkoxy group, a C1-C4 alkylenedioxy group, a C1-C6 alkylsulfonyl group, a halogen substituted or unsubstituted C1-C6 alkylthio group, a nitro group, and an amino group which may have a C1-C6 alkanoyl group as a substituent, may be substituted]; a benzofuryl group [wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted]; a biphenylyl group; a furyl group [wherein, on the furan ring, a phenyl group which may have a halogen atom as a substituent may be substituted]; or a thiazolyl group [wherein on the thiazole ring, at least one phenyl group which may have a halogen atom may be substituted]);

(Ff4) a phenyl group (wherein, on the phenyl ring, at least one selected from the following group may be substituted: a halogen atom; a halogen substituted or unsubstituted C1-C6 alkyl group; a C3-C8 cycloalkyl group; a hydroxyl group; a halogen substituted or unsubstituted C1-C8 alkoxy group; a C3-C8 cycloalkoxy group; a C1-C4 alkylenedioxy group; a cyano group; a nitro group; a phenyl C2-C6 alkenyl group; a C2-C6 alkanoyloxy group; an amino group which may have a C1-C6 alkanoyl group as a substituent; a C1-C6 alkylsulfonylamino group; a phenyl C1-C6 alkoxy group; a phenoxy group; an amino group wherein at least one C1-C6 alkyl group is substituted; an amino group wherein at least one phenyl group is substituted; an amino C1-C6 alkoxy group [wherein, on the amino group, at least one C1-C6 alkyl group may be substituted]; a C1-C6 alkoxycarbonyl group; a C1-C6 alkoxycarbonylC1-C6 alkoxy group; a C1-C6 alkylthio group; a pyrolyl group; an imidazolyl group; a piperidyl group; a morpholino group; a pyrrolidinyl group; a thienyl group; a benzofuryl group; a piperazinyl group [wherein, on the piperazine ring, at least one selected from the group consisting of a C1-C6 alkyl group, a phenyl C1-C6 alkyl group, and a benzoyl group which may have at least one C1-C6 alkyl group, may be substituted as a substituent]; a quinolyl group [wherein, on the quinoline ring, at least one selected from the group consisting of a C1-C6 alkoxy group and an oxo group may be substituted]; a piperidylcarbonyl group wherein, on the piperidine ring, a carbostyril group may be substituted; and a triazolyl group);

(Ff5) a naphthyl group (wherein, on the naphthalene ring, at least one selected from the group consisting of a halogen atom, a halogen substituted or unsubstituted C1-C6 alkoxy group, and an amino group which may have a C1-C6 alkyl group as a substituent, may be substituted);

(Ff6) a biphenylyl group (wherein, on the biphenylyl ring, at least one selected from the group consisting of a halogen atom, a halogen substituted or unsubstituted C1-C9 alkyl group, and a halogen substituted or unsubstituted C1-C6 alkoxy group, may be substituted);

(Ff7) a fluorenyl group; a pyrenyl group;

(Ff8) a benzofuryl group (wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted);

(Ff9) a benzothienyl group (wherein, on the benzothiophene ring, at least one selected from the group consisting of a halogen atom, a halogen substituted or unsubstituted C1-C6 alkyl group, and a halogen substituted or unsubstituted C1-C6 alkoxy, group, may be substituted);

(Ff10) a pyridyl group (wherein, on the pyridine ring, at least one selected from the group consisting of a halogen atom, a halogen substituted or unsubstituted C1-C6 alkyl group, a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], a furyl group, and a thienyl group, may be substituted);

(Ff11) a furyl group (wherein, on the furan ring, 1 to 3 groups selected from the group consisting of a C1-C6 alkyl group, a nitro group, and a phenyl group [wherein, on the phenyl ring, at least one selected from the group consisting of a halogen atom, a halogen substituted or unsubstituted C1-C6 alkyl group, a halogen substituted or unsubstituted C1-C6 alkoxy group, and a nitro group, may be substituted], may be substituted);

(Ff12) a benzothiazole group (wherein, on the benzothiazole ring, at least one phenyl group, which may have, as a substituent, a C1-C6 alkoxy group on the phenyl ring, may be substituted);

(Ff13) a thienyl group (wherein, on the thiophene ring, at least one selected from the group consisting of a halogen atom, a nitro group, a C1-C6 alkyl group, a pyrazolyl group wherein, on the pyrazole ring, at least one halogen substituted or unsubstituted C1-C6 alkyl group may be substituted, and a thienyl group wherein, on the thiophene ring, a halogen atom may be substituted, may be substituted);

(Ff14) an indolyl group (wherein, on the indole ring, at least one selected from the group consisting of a phenylsulfonyl group which may have a C1-C6 alkyl group as a substituent, a phenyl C1-C6 alkyl group, a C1-C6 alkoxycarbonyl group, and a phenyl group, may be substituted);

(Ff15) a pyrrolyl group (wherein, on the pyrrole ring, at least one selected from the group consisting of a phenyl group wherein at least one halogen substituted or unsubstituted C1-C6 alkyl group may be substituted and a C1-C6 alkyl group may be substituted);

(Ff16) a coumaryl group;

(Ff17) a benzoimidazolyl group (wherein, on the benzoimidazole ring, at least one thienyl group may be substituted);

(Ff18) an oxazolyl group (wherein, on the oxazole ring, at least one phenyl group which may have a halogen atom may be substituted);

(Ff19) a thiazolyl group (wherein, on the thiazole ring, at least one phenyl group may be substituted, and further wherein, on the phenyl ring, at least one selected from the group consisting of a halogen atom, a nitro group, and a phenyl group, may be substituted);

(Ff21) a quinolyl group;

(Ff22) a 3,4-dihydrocarbostyril group (wherein, on the 3,4-dihydrocarbostyril ring, at least one selected from the group consisting of a C1-C6 alkoxy group, a C1-C6 alkyl group, and a phenyl C1-C6 alkoxy group, may be substituted); a carbostyril group (wherein, on the carbostyril ring, at least one selected from the group consisting of a C1-C6 alkoxy group, a C1-C6 alkyl group, and a phenyl C1-C6 alkoxy group, may be substituted);

(Ff23) an imidazo[2,1-b]thiazolyl group;

(Ff24) an imidazo[2,1-a]pyridyl group;

(Ff25) a chromanyl group (wherein, on the chromane ring, at least one C1-C6 alkyl group may be substituted); or (Ff26) a 2,3-dihydrobenzofuryl group); or (Fd39) a group represented by general formula (Ffb):

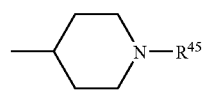

(Ffb)

(wherein $R^{45}$ represents: a C1-C6 alkoxycarbonyl group; a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; an amino substituted C1-C6 alkyl group [wherein, on the amino group, at least one selected from the group consisting of a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) and a C1-C6 alkyl group may be substituted]; a benzoyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a phenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a phenyl C1-C6 alkoxycarbonyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; or a phenyl C2-C6 alkenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]));

F12-3) a morpholino group;

F12-4) an imidazolyl group;

F12-5) a 1,4-dioxazaspiro[4,5]decyl group (wherein, on the 1,4-dioxazaspiro[4,5]decane ring, at least one oxo group may be substituted);

F12-6) a homopiperazinyl group (wherein, on the homopiperazine ring, at least one selected from the group consisting of a C1-C6 alkoxycarbonyl group, a phenyl C1-C6 alkoxycarbonyl group, and a phenyl substituted or unsubstituted phenyl group, may be substituted);

F12-7) a piperazinyl group (wherein, on the piperazine ring, at least one selected from the group consisting of an oxo group, a C1-C6 alkyl group, and a phenyl C1-C6 alkyl group [wherein, on the phenyl ring, at least one halogen substituted or unsubstituted C1-C6 alkyl group may be substituted], may be substituted);

F12-8) a piperidyl group (wherein, on the piperidine ring, at least one oxo group may be substituted);

F12-9) a pyrrolidinyl group (wherein, on the pyrrolidine ring, at least one phenoxy C1-C6 alkyl group, which may have a halogen substituted or unsubstituted C1-C6 alkoxy group as a substituent, may be substituted); or F12-10) an isoindolinyl group; or further F13) $R^{19}$ and $R^{20}$ may bind to each other together with nitrogen atoms adjacent thereto directly or through heteroatoms, so as to form a cyclic imide or amide represented by any one of the following (F13-1) to (F13-11):

(F13-1) a succinimide group;

(F13-2) an oxazolidinyl group (wherein, on the oxazolidine ring, at least one oxo group may be substituted);

(F13-3) a benzo-1,3-oxazolidinyl group (wherein, on the benzo-1,3-oxazolidine ring, at least one selected from the group consisting of an oxo group, a halogen atom, and a phenyl group, may be substituted);

(F13-4) an imidazolidinyl group (wherein, on the imidazolidine ring, at least one selected from the group consisting of an oxo group, a phenyl C1-C6 alkyl group [wherein, on the phenyl ring, 1 to 3 groups selected from the group consisting of a halogen atom and a C1-C6 alkoxy group may be substituted], and a phenyl group, may be substituted);

(F13-5) a benzoimidazolidinyl group (wherein, on the benzoimidazolidine ring, at least one selected from the group consisting of an oxo group, a halogen atom, a halogen substituted or unsubstituted C1-C6 alkyl group, an amino group which may have a C1-C6 alkyl group as a substituent, a C1-C6 alkoxycarbonyl group, and a piperidyl group [wherein, on the piperidine ring, at least one selected from the group consisting of a C1-C6 alkyl group, a phenyl group wherein, on the phenyl ring, 1 to 3 halogen atoms may be substituted, a C1-C6 alkoxycarbonyl group, and a phenyl C1-C6 alkoxycarbonyl group, may be substituted], may be substituted);

(F13-6) a phthalimide group;

(F13-7) an indolinyl group (wherein, on the indoline ring, at least one selected from the group consisting of a C1-C6 alkyl group, a halogen atom, and an oxo group, may be substituted);

(F13-8) a 2,3-dihydrobenzothiazolyl group (wherein, on the 2,3-dihydrobenzothiazole ring, at least one oxo group may be substituted);

(F13-9) a 1H-2,4-benzoxazinyl group (wherein, on the 1H-2,4-benzoxazine ring, at least one oxo group may be substituted);

(F13-10) a group represented by general formula (Fga):

(Fga)

(wherein $R^{39}$ represents: a hydrogen atom; a phenyl C1-C6 alkyl group which may have, as a substituent, a halogen atom on the phenyl ring; a phenoxy C1-C6 alkyl group which may have, as a substituent, a halogen atom on the phenyl ring; a phenyl C2-C6 alkenyl group which may have, as a substituent, a halogen atom on the phenyl ring; a phenyl group wherein, on the phenyl ring, at least one selected from the group consisting of a halogen atom, a halogen substituted or unsubstituted C1-C6 alkyl group, a halogen substituted or unsubstituted C1-C6 alkoxy group, and a phenyl group, may be substituted as a substituent; a pyridyl group; or a pyrazinyl group); or (F13-11) a 1,3-thiazolidinyl group (wherein, on the 1,3-thiazolidine ring, at least one selected from the group consisting of an oxo group and a phenyl C1-C6 alkylidene group which may have a halogen substituted or unsubstituted C1-C6 alkyl group on the phenyl ring, may be substituted as a substituent).

A group represented by general formula (G):

(G)

(wherein $R^{40}$ represents a C1-C6 alkyl group or a halogen substituted or unsubstituted phenyl group).

The reaction between a compound (10a) or (10b) and a compound (11) is carried out in a suitable solvent or in no solvents, in the presence or absence of a basic compound.

Examples of a solvent used herein may include: water; alcohols such as methanol, ethanol, isopropanol, n-butanol, or tert-butanol; aromatic hydrocarbons such as benzene, toluene, xylene, tetralin, o-chlorobenzene, m-chlorobenzene, or 2,3-dichlorobenzene; halogenated hydrocarbons such as dichloromethane, dichloroethane, chloroform, or carbon tetrachloride; ethers such as diethyl ether, dimethoxyethane, dioxane, tetrahydrofuran, diglime, or dipropyl ether; saturated hydrocarbons such as n-hexane, n-butane, cyclohexane, or liquid paraffin; ketones such as acetone or methyl ethyl ketone; polar solvents such as N-N-dimethylformamide, dimethyl sulfoxide, hexamethyl phosphoric triamide, acetonitrile, N-N-dimethylacetamide, or NMP; and their mixed solvents.

Known inorganic bases and organic bases can widely be used as basic compounds.

Examples of an inorganic base may include: alkali metal carbonates such as sodium carbonate or potassium carbonate; alkali metal hydrogencarbonates such as sodium bicarbonate or potassium bicarbonate; alkali metal hydroxides such as sodium hydroxide or potassium hydroxide; alkali metal phosphates such as sodium phosphate or potassium phosphate; alkali metal hydrides such as sodium hydride or potassium hydride; alkali metals such as potassium or sodium; alkali metal amidates such as sodium amide; and alkali metal alcoholates such as sodium methylate, sodium ethylate, or sodium tert-butoxide.

Examples of an organic base may include acetates such as sodium acetate or potassium acetate, pyridine, trimethylamine, triethylamine, diisopropylethylamine, dimethyl aniline, 1-methylpyrrolidine, N-methylmorpholine, N,N-dimethyl-4-aminopyridine, 1,5-diazabicyclo[4.3.0]nonen-5 (DBN), 1,8-diazabicyclo[5.4.0]undecen-7 (DBU), and 1,4-diazabicyclo[2.2.2]octan (DABCO).

The compound (11) is used to 1 mole of the compound (10a) or (10b) at an amount of generally at least 1 mole, and preferably between 1 and 5 moles.

The basic compound is used to 1 mole of the compound (10a) or (10b) at an amount generally between 0.1 and 1 mole, and preferably between 0.1 and 0.5 moles.

The reaction between the compound (10a) or (10b) and the compound (11) is carried out at a temperature generally between room temperature and 150° C., and preferably between room temperature and 120° C. It is generally carried out for 10 minutes to 24 hours before termination.

The reaction to obtain a compound (13a) from a compound (12a) and the reaction to obtain a compound (13b) from a compound (12b) are carried out in a suitable solvent or in no solvents, in the presence of a basic compound.

All the solvents and basic compounds that can be used in the aforementioned reaction between the compound (10a) or (10b) and the compound (11) can be used also herein as solvents and basic compounds.

The basic compound is used to 1 mole of the compound (12a) or (12b) at an amount of generally at least 1 mole, and preferably between 1 and 2 moles.

The above reaction is carried out at a temperature generally between 0° C. and 150° C., and preferably between 0° C. and 120° C. It is generally carried out for 10 minutes to 48 hours before termination.

Among the 4-nitroimidazole compounds represented by general formula (1) of the present invention, those having a basic group can easily form a salt together with generally pharmacologically acceptable acid. Examples of such acid may include: inorganic acids such as sulfuric acid, nitric acid, hydrochloric acid, phosphoric acid, or hydrobromic acid; and organic acids such as acetic acid, p-toluenesulfonic acid, methanesulfonic acid, ethanesulfonic acid, oxalic acid, maleic acid, fumaric acid, citric acid, succinic acid, malic acid, tartaric acid, malonic acid, lactic acid, or benzoic acid.

A compound of interest obtained as a result of each of the above reactions is separated from the reaction mixture by common separation means, and it can further be purified. Examples of such separation and purification means may include distillation, recrystallization, column chromatography, ion exchange chromatography, gel chromatography, affinity chromatography, preparative thin layer chromatography, and the solvent extraction method.

According to the present invention, the compound of interest represented by general formula (1) can be produced without passing the state of an intermediate, which has a danger of explosion.

The production method of the present invention involves simple operations, and it does not need a complicated purification process.

According to the production method of the present invention, the 4-nitroimidazole compound of interest represented by general formula (1) can be economically produced at high yield and at high purity.

Accordingly, the method of the present invention is industrially extremely advantageous.

The present invention will be more specifically described in the following examples.

REFERENCE EXAMPLE 1

Production of 2,5-dibromo-4-nitroimidazole

A mixture consisting of 4-nitroimidazole (100 g, 884 mmol), sodium bicarbonate (164 g, 1.94 mol), and water (500 ml) was intensively stirred, and thereafter, bromine (106 ml, 2.07 mol) was added dropwise to the mixture at room temperature (23° C. to 25° C.) over 6 hours (wherein it intensively foamed during the dropping). The thus obtained mixture was further stirred under heating (50° C. to 55° C., 4 hours). Thereafter, water (400 ml) and concentrated hydrochloric acid (80 ml) were added thereto under cooling on ice (10° C. or lower), and the obtained mixture was stirred for 1 hours. Crystals were collected by filtration. The obtained crystals were washed with water (on a filter paper, with 400 ml of water), dispersedly washed (with 800 ml of water, twice), and air-dried (50° C., 16 hours).

Yield: 213 g (Yield: 88.9%), pale yellow crystal IR (KBr): 3074, 1548, 1468, 1392, 1361, 1345, 1310, 1259, 1172, 1066, 975, 830, 667 $cm^{-1}$.

REFERENCE EXAMPLE 2

Production of 2,5-dichloro-4-nitroimidazole

A mixture consisting of 2,5-dibromo-4-nitroimidazole (27.1 g, 100 mmol) and concentrated hydrochloric acid (434 ml) was stirred under heating (77° C. to 80° C., 16 hours). The reaction mixture was left to cool, and then stirred under cooling on ice (5° C. to 10° C., 2 hours). Thereafter, the precipitated crystals were collected by filtration and air-dried (50° C., 5 hours). The yield of the dried product was 8.26 g. The filtrate was further extracted with ethyl acetate (300 ml) and then dried ($MgSO_4$), followed by vacuum concentration and exsiccation. The yield of the exsiccated product was 9.63 g. Thus, 17.9 g (in total) of 2,5-dichloro-4-nitroimidazole was obtained (yield: 98.3%).

IR (KBr): 1566, 1475, 1403, 1366, 1332, 1272, 1190, 1091, 996, 834, 679 $cm^{-1}$. MS (70 eV) m/z (relative intensity): 183 (15, $M^+$), 181 (25), 108 (28), 74 (42), 62 (100).

EXAMPLE 1

Production of 2-chloro-5-iodo-4-nitroimidazole

A suspension consisting of 2,5-dichloro-4-nitroimidazole (7.66 g, 42.1 mmol), sodium iodide (75.7 g, 505 mmol), and water (77 ml) was heated to reflux (102° C., 35 hours). The reaction mixture was cooled to room temperature. Thereafter, crystals were collected by filtration, washed with water (on a filter paper, 77 ml), and then air-dried (50° C., 20 hours).

Yield: 9.36 g (Yield: 81.3%), pale yellow crystal IR (KBr): 3199, 1538, 1468, 1394, 1346, 1300, 1262, 1166, 1049, 986, 831, 756, 734, 674 cm$^{-1}$ MS (70 eV) m/z (relative intensity) : 274 (34, M$^+$), 273 (100), 166 (35), 154 (80).

EXAMPLE 2

Production of 2-bromo-5-iodo-4-nitroimidazole

A suspension consisting of 2,5-dibromo-4-nitroimidazole (27.1 g, 100 mmol), sodium iodide (150 g, 1.00 mol), and water (271 ml) was heated to reflux (102° C., 15 hours). The reaction mixture was cooled to room temperature. Thereafter, crystals were collected by filtration, washed with water (on a filter paper, 270 ml), and then air-dried (50° C., 20 hours).

Yield: 29.0 g (Yield: 91.2%), pale yellow crystal IR (KBr): 3218, 1537, 1456, 1386, 1336, 1288, 1250, 1156, 1048, 969, 829, 756, 731, 665 cm$^{-1}$ MS (70 eV) m/z (relative intensity): 319 (80, M$^+$), 317 (82), 154 (100), 106 (78).

EXAMPLE 3

Production of 2-bromo-5-iodo-4-nitroimidazole

A suspension consisting of 2,5-dibromo-4-nitroimidazole (2.71 g, 10.0 mmol), sodium iodide (15.0 g, 100 mmol), tetrabutylammonium iodide (185 mg, 0.50 mmol), and water (27 ml) was stirred under heating (80° C. to 85° C., 27 hours). The reaction mixture was cooled to room temperature. Thereafter, crystals were collected by filtration, washed with water (on a filter paper, 27 ml), and then air-dried (50° C., 18 hours).

Yield: 2.71 g (Yield: 85.3%), pale yellow crystal IR (KBr): 3218, 1537, 1456, 1386, 1336, 1288, 1250, 1156, 1048, 969, 829, 756, 731, 665 cm$^{-1}$ MS (70 eV) m/z (relative intensity): 319 (80, M$^+$), 317 (82), 154 (100), 106 (78).

EXAMPLE 4

Production of 2-bromo-5-iodo-4-nitroimidazole

A suspension consisting of 2,5-dibromo-4-nitroimidazole (2.71 g, 10.0 mmol), sodium iodide (15.0 g, 100 mmol), water (27 ml), and a 57% hydriodic acid aqueous solution (5.4 ml) was stirred under heating (50° C. to 60° C., 56 hours). The reaction mixture was cooled to room temperature. Thereafter, crystals were collected by filtration, washed with water (on a filter paper, 27 ml), and then air-dried (50° C., 15 hours)

Yield: 2.43 g (Yield: 76.4%), pale yellow crystal IR (KBr): 3218, 1537, 1456, 1386, 1336, 1288, 1250, 1156, 1048, 969, 829, 756, 731, 665 cm$^{-1}$ MS (70 eV) m/z (relative intensity): 319 (80, M$^+$), 317 (82), 154 (100), 106 (78).

EXAMPLE 5

Production of 2-bromo-5-iodo-4-nitroimidazole

A suspension consisting of 2,5-dibromo-4-nitroimidazole (2.71 g, 10.0 mmol), water (13.6 ml), and a 57% hydriodic acid aqueous solution (13.6 ml) was stirred under heating (50° C. to 60° C., 36 hours). The reaction mixture was cooled to room temperature. Thereafter, crystals were collected by filtrations washed with water (on a filter paper, 27 ml), and then air-dried (50° C., 15 hours)

Yield: 1.11 g (Yield: 34.9%), pale yellow crystal IR (KBr): 3218, 1537, 1456, 1386, 1336, 1288, 1250, 1156, 1048, 969, 829, 756, 731, 665 cm$^{-1}$ MS (70 eV) m/z (relative intensity): 319 (80, M$^+$), 317 (82), 154 (100), 106 (78).

EXAMPLE 6

Production of 2-chloro-4-nitroimidazole

A mixture consisting of 2-chloro-5-iodo-4-nitroimidazole (273 mg, 1.00 mmol), ethanol (2.7 ml), triethylamine (443 mg, 3.00 mmol), and platinum oxide (2.9 mg, 1.1 wt %) was stirred under normal pressure in a hydrogen atmosphere at room temperature for 2 hours. The filtrate was concentrated and exsiccated under reduced pressure, and the residue was then dissolved in ethyl acetate (30 ml). The organic layer was washed with 3% diluted hydrochloric acid (10 ml) and saturated saline (5 ml, twice), and then dried (MgSO$_4$), followed by vacuum concentration and exsiccation.

Yield: 144 mg (Yield: 97.6%) IR (KBr): 1556, 1510, 1472, 1404, 1375, 1358, 1193, 1093, 998, 979, 822, 753, 679, 595, 523 cm$^{-1}$ NMR (DMSO-d$_6$) δ ppm: 8.40 (s, 1H), 14.2 (br, s, 1H).

EXAMPLE 7

Production of 2-bromo-4-nitroimidazole

A mixture consisting of 2-bromo-5-iodo-4-nitroimidazole (607 mg, 2.00 mmol), ethanol (6.4 ml), triethylamine (607 mg, 6.00 mmol), and platinum oxide (3.4 mg, 0.53 wt %) was stirred under normal pressure in a hydrogen atmosphere at room temperature for 3 hours. The filtrate was concentrated and exsiccated under reduced pressure, and the residue was then dissolved in ethyl acetate (50 ml). The organic layer was washed with 3% diluted hydrochloric acid (10 ml) and saturated saline (10 ml, twice), and then dried (MgSO$_4$), followed by vacuum concentration and exsiccation.

Yield: 365 mg (Yield: 95.1%) IR (KBr): 1548, 1514, 1453, 1392, 1373, 1258, 1168, 1085, 968, 823, 799, 751, 668 cm$^{-1}$ NMR (DMSO-d$_6$) δ ppm: 8.45 (s, 1H), 14.1 (br, s, 1H).

EXAMPLE 8

Production of 2-bromo-4-nitroimidazole

A mixture consisting of 2-bromo-5-iodo-4-nitroimidazole (636 mg, 2.00 mmol), ethanol (6.4 ml), triethylamine (607 mg, 6.00 mmol), and 2% Pd alumina (95.4 mg, 15 wt %) was stirred under normal pressure in a hydrogen atmosphere at 50° C. to 60° C. for 15 hours. The filtrate was concentrated and exsiccated under reduced pressure, and the residue was then dissolved in ethyl acetate (50 ml). The organic layer was washed with 3% diluted hydrochloric acid (10 ml) and saturated saline (10 ml, twice), and then dried (MgSO$_4$), followed by vacuum concentration and exsiccation.

Yield: 364 mg (Yield: 94.8%) IR (KBr): 1548, 1514, 1453, 1392, 1373, 1258, 1168, 1085, 968, 823, 799, 751, 668 cm$^{-1}$ NMR (DMSO-d$_6$) δ ppm: 8.45 (s, 1H), 14.1 (br, s, 1H).

EXAMPLE 9

Production of 2-bromo-4-nitroimidazole

A mixture consisting of 2-bromo-5-iodo-4-nitroimidazole (1.27 g, 4.00 mmol), ethanol (13 ml), triethylamine (1.21 g, 12.0 mmol), and 2% Pd alumina (191 mg, 15 wt %) was stirred while applying pressure (3 to 4 atmospheres) in a hydrogen atmosphere at room temperature for 14 hours. The filtrate was concentrated and exsiccated under reduced pressure, and the residue was then dissolved in ethyl acetate (100 ml). The organic layer was washed with 3% diluted hydrochloric acid (30 ml) and saturated saline (20 ml, twice), and then dried (MgSO$_4$), followed by vacuum concentration and exsiccation.

Yield: 761 mg (Yield: 99.1%) IR (KBr): 1548, 1514, 1453, 1392, 1373, 1258, 1168, 1085, 968, 823, 799, 751, 668 cm$^{-1}$ NMR (DMSO-d$_6$) δ ppm: 8.45 (s, 1H), 14.1 (br, s, 1H).

EXAMPLE 10

Production of 2-bromo-4-nitroimidazole

Tetra-n-butyl ammonium borohydride (602 mg, 2.34 mmol) was added to a solution obtained by dissolving 2-bromo-5-iodo-4-nitroimidazole (186 mg, 0.585 mmol) in dried dixane (2.8 ml). The obtained mixture was stirred at 60° C. for 28 hours. The reaction mixture was cooled to room temperature, and it was then poured into 10% diluted hydrochloric acid (10 ml). The reaction product was extracted with ethyl acetate, and the ethyl acetate extract solution (40 ml) was dried (MgSO$_4$), followed by vacuum concentration and exsiccation.

Yield: 86 mg (Yield: 76.6%) IR (KBr): 1548, 1514, 1453, 1392, 1373, 1258, 1168, 1085, 968, 823, 799, 751, 668 cm$^{-1}$ NMR (DMSO-d$_6$) δ ppm: 8.45 (s, 1H), 14.1 (br, s, 1H).

EXAMPLE 11

Production of 2-bromo-4-nitroimidazole

A mixture consisting of 2-bromo-5-iodo-4-nitroimidazole (2.43 g, 7.64 mmol), isopropyl alcohol (12.2 ml), water (2.4 ml), triethylamine (2.32 g, 22.9 mmol), and 5% Pd-alumina (12.2 mg) was stirred while applying pressure (3 to 4 atmospheres) in a hydrogen atmosphere at 60° C. for 3 hours. The filtrate was concentrated and exsiccated under reduced pressure, and the resultant product was then dissolved in water (10 ml). The thus obtained solution was treated with activated carbon (243 mg) (which was stirred at room temperature for 1 hour). The filtrate was stirred under cooling on ice, and 35% concentrated hydrochloric acid (0.7 ml) was added thereto such that the pH of the solution became 2. The thus obtained solution was further stirred under cooling on ice for 1 hour. Thereafter, the precipitated crystals were collected by filtration and then dried at 50° C. for 16 hours.

Yield: 1.14 g (Yield: 77.7%) NMR (DMSO-d$_6$) δ ppm: 8.42 (s, 1H), 14.1 (br, s, 1H).

EXAMPLE 12

Production of 2-bromo-4-nitroimidazole

2-Bromo-5-iodo-4-nitroimidazole (1.00 g, 3.15 mmol) was dissolved in dimethylformamide (8 ml) and water (3 ml). The obtained solution was stirred under cooling on ice, and then, a 50% to 55% ammonium bisulfite aqueous solution (3.6 ml, 23.5 mmol with a content of 52.5%) was added thereto. The obtained mixture was stirred at room temperature for 3 days. Thereafter, cold water (30 ml) was added to the reaction product, followed by extraction with ethyl acetate 3 times (167 ml in total). The organic layer was washed with 5% saline twice and then dried (MgSO$_4$), followed by vacuum concentration and exsiccation.

Yield: 375 mg (Yield: 62.1%) NMR (DMSO-d$_6$) δ ppm: 8.44 (s, 1H). 14.1 (br, s, 1H).

EXAMPLE 13

Production of 2-bromo-4-nitroimidazole

2-Bromo-5-iodo-4-nitroimidazole (1.54 g, 4.84 mmol) was dissolved in dimethylformamide (12.3 ml) and water (6.2 ml). Thereafter, sodium sulfite (1.22 g, 9.70 mmol) was added to the obtained solution. The mixture was heated to a temperature between 40° C. and 60° C., and it was then stirred at the temperature for 20 hours. Thereafter, sodium sulfite (2.44 g, 19.4 mmol) was further added to the reaction solution, and the obtained mixture was stirred at 60° C. for 15 hours. The reaction mixture was cooled to room temperature, and then, diluted hydrochloric acid was added thereto, followed by extraction with ethyl acetate (3 times, 200 ml in total). The organic layer was dried (MgSO$_4$), and water (10 ml) was added to the oil-state residue obtained by concentration. The precipitated crystals were collected by filtration, and then dried at 60° C. for 15 hours.

Yield: 349 mg (Yield: 37.5%) IR (KBr): 3201, 3146, 1547, 1514, 1452, 1391, 1373, 1356, 1258, 1167, 1084, 968, 823, 798, 750, 668 cm$^{-1}$ NMR (DMSO-d$_6$) δ ppm: 8.43 (s, 1H). 14.1 (br, s, 1H).

EXAMPLES 14 TO 19

2-Bromo-4-nitroimidazole was produced in the same manner as in Example 12 with the exceptions that sulfites and solvents shown in Table 1 indicated below were used, and that the reaction temperature and the reaction time were determined as shown in Table 1 indicated below. The yields of 2-bromo-4-nitroimidazole are also shown in Table 1. In the table, the amount of sulfite used (mole) is a value determined using 1 mole of 2-bromo-5-iodo-4-nitroimidazole as a standard. In addition, the amount of a solvent (dimethylformamide (DMF), water, or 1-methyl-2-pyrrolidinone (NMP)) used is a value determined using 1 millimole of 2-bromo-5-iodo-4-nitroimidazole as a standard.

TABLE 1

| Example NO. | Sulfite (mole) | Solvent (ml) | Reaction temperature (° C.) | Reaction time (hour) | Yield (%) |
|---|---|---|---|---|---|
| 14 | Sodium sulfite (6.0 moles) | DMF 2.4 ml Water 0.8 ml | 65-70 | 31 | 40.0 |
| 15 | Sodium bisulfite (4.6 moles) | DMF 2.5 ml Water 1.3 ml | 50 | 20 | 47.6 |
| 16 | Sodium pyrosulfite (4.0 moles) | DMF 2.5 ml Water 1.3 ml | 50 | 24 | 43.9 |
| 17 | Ammonium sulfite monohydrate (4.0 moles) | DMF 2.5 ml Water 1.3 ml | 50 | 18 | 49.5 |
| 18 | 50% to 55% ammonium bisulfite aqueous solution (7.4 moles) | DMF 2.5 ml Water 1.0 ml | 25 | 96 | 62.1 |
| 19 | 50% to 55% ammonium bisulfite aqueous solution (7.3 moles) | NMP 1.6 ml | 25 | 72 | 65.9 |

EXAMPLE 20

Production of 2-bromo-5-iodo-4-nitroimidazole

A mixture consisting of 2,5-dibromo-4-nitroimidazole (108.3 g, 400 mmol), ethanol (184 ml), sodium iodide (120 g, 800 mmol) was heated to reflux in an argon stream (65-70° C., 26 hours). The reaction mixture was cooled to room temperature and the precipitated inorganic salt was removed by filtration. 78% (234 ml) of the filtrate (300 ml) was concentrated and exsiccated under reduced pressure (25-50° C.). The residue (brown oil, 172 g) was suspended in chilled water (422 ml), and concentrated hydrochloric acid (10 ml) was added thereto such that the pH of the solution became 1 to 2. The thus obtained solution was further stirred under cooling on ice for 2 hours. Thereafter, the precipitated crystals were collected by filtration and then dried at 50° C. for 24 hours.

Yield: 89.2 g (Yield: 89.9%), pale yellow crystal IR (KBr): 3218, 1537, 1456, 1386, 1336, 1288, 1250, 1156, 1048, 969, 829, 756, 731, 665 cm$^{-1}$ MS (70 eV) m/z (relative intensity): 319 (80, M$^+$), 317 (82), 154 (100), 106 (78).

The invention claimed is:

1. A method for producing a 4-nitroimidazole compound represented by general formula (1):

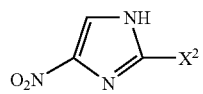

(1)

wherein X$^2$ represents a chlorine atom or bromine atom, comprising iodinating a 4-nitroimidazole compound represented by general formula (2):

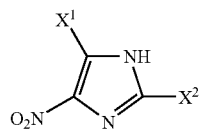

(2)

wherein each of X$^1$ and X$^2$ represents a chlorine atom or bromine atom in a suitable solvent in the presence of an iodinating agent, and then reducing the obtained 5-iodo-4-nitroimidazole compound represented by general formula (3):

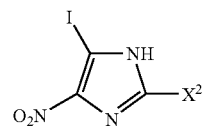

(3)

wherein X$^2$ is the same as defined above in an appropriate solvent in the presence of a reducing agent.

2. The production method according to claim 1, wherein the iodinating agent is a halogen molecule, hydriodic acid, or a metal salt of hydriodic acid.

3. The production method according to claim 2, wherein the metal salt of hydriodic acid is sodium iodide, potassium iodide, lithium iodide, zinc iodide, magnesium iodide, or aluminum iodide.

4. The production method according to claim 3, wherein the iodinating agent is used to the compound (2) at a molar ratio between 1.5:1 and 15:1, and the iodinating agent is sodium iodide.

5. The production method according to claim 1, wherein the reaction is carried out in the presence of a phase-transfer catalyst.

6. The production method according to claim 5, wherein the phase-transfer catalyst is used to the compound (2) at a molar ratio between 0.01:1 and 1:1, and the phase-transfer catalyst is a quaternary ammonium salt, phosphonium salt, or pyridinium salt.

7. The production method according to claim 1, wherein the reducing agent is a hydrogenation reducing agent, and the reducing agent is used to the compound (3) at a molar ratio between 1:1 and 10:1.

8. The production method according to claim 1, wherein the reducing agent is a catalytic hydrogenation reducing agent, and the reducing agent is used to the compound (3) at a weight ratio between 0.1% by weight and 40% by weight.

9. The production method according to claim 8, wherein the reaction is carried out in the presence of triethylamine, trimethylamine, or N-ethyldiisopropylamine.

\* \* \* \* \*